(12) United States Patent
Klar et al.

(10) Patent No.: US 9,096,639 B2
(45) Date of Patent: Aug. 4, 2015

(54) 17-HYDROXY-17-PENTAFLUORETHYL-ESTRA-4,9(10)-DIEN-11-ACYLOXYALKYLENE PHENYL DERIVATIVES, METHODS FOR THE PRODUCTION THEREOF AND USE THEREOF FOR TREATING DISEASES

(75) Inventors: Ulrich Klar, Berlin (DE); Wolfgang Schwede, Glienicke (DE); Carsten Moller, Berlin (DE); Andrea Rotgeri, Berlin (DE); Ursula Krenz, Leichlingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 623 days.

(21) Appl. No.: 13/384,332

(22) PCT Filed: Jul. 7, 2010

(86) PCT No.: PCT/EP2010/004148
§ 371 (c)(1),
(2), (4) Date: Jun. 4, 2012

(87) PCT Pub. No.: WO2011/009530
PCT Pub. Date: Jan. 27, 2011

(65) Prior Publication Data
US 2012/0232042 A1    Sep. 13, 2012

(30) Foreign Application Priority Data
Jul. 20, 2009 (DE) .................. 10 2009 034 368

(51) Int. Cl.
| | | |
|---|---|---|
| A61K 31/56 | (2006.01) |
| A61K 31/58 | (2006.01) |
| C07J 11/00 | (2006.01) |
| C07J 41/00 | (2006.01) |
| C07J 1/00 | (2006.01) |
| C07J 7/00 | (2006.01) |
| C07J 43/00 | (2006.01) |
| A61K 31/573 | (2006.01) |

(52) U.S. Cl.
CPC .............. *C07J 1/0081* (2013.01); *C07J 7/0085* (2013.01); *C07J 41/0044* (2013.01); *C07J 41/0083* (2013.01); *C07J 43/003* (2013.01); *A61K 31/573* (2013.01); *A61K 31/58* (2013.01)

(58) Field of Classification Search
CPC .... C07J 7/0085; C07J 41/0083; C07J 43/003; A61K 31/573; A61K 31/58
USPC ................... 514/176, 179; 552/517, 519, 648
See application file for complete search history.

(56) References Cited

U.S. PATENT DOCUMENTS

| | | |
|---|---|---|
| 4,386,085 A | 5/1983 | Teutsch et al. |
| 4,519,946 A | 5/1985 | Teutsch et al. |
| 4,609,651 A | 9/1986 | Rohde et al. |
| 4,634,695 A | 1/1987 | Torelli et al. |
| 4,900,725 A | 2/1990 | Nioue et al. |
| 4,921,846 A | 5/1990 | Nedelec et al. |
| 4,954,490 A | 9/1990 | Cook et al. |
| 5,073,548 A | 12/1991 | Cook et al. |
| 5,108,996 A | 4/1992 | Claussner et al. |
| 5,272,140 A | 12/1993 | Loozen |
| 5,407,928 A | 4/1995 | Kasch et al. |
| 5,576,310 A | 11/1996 | Schubert et al. |
| 5,693,628 A | 12/1997 | Schubert et al. |
| 5,712,264 A | 1/1998 | Hamersma et al. |
| 5,739,125 A | 4/1998 | Kasch et al. |
| 5,986,115 A | 11/1999 | Bohlmann et al. |
| 6,020,328 A | 2/2000 | Cook et al. |
| 6,043,234 A | 3/2000 | Stöckemann et al. |
| 6,225,298 B1 | 5/2001 | Spicer et al. |
| 6,316,432 B1 | 11/2001 | Schwede et al. |
| 6,476,079 B1 | 11/2002 | Jukarainen et al. |
| 6,503,895 B2 | 1/2003 | Schwede et al. |
| 6,806,263 B2 | 10/2004 | Schwede et al. |
| 6,825,182 B2 | 11/2004 | Ring et al. |
| 6,861,415 B2 | 3/2005 | Kim et al. |
| 7,087,591 B2 | 8/2006 | Kim et al. |
| 7,148,213 B2 | 12/2006 | Schwede et al. |
| 7,192,942 B2 | 3/2007 | Grawe et al. |
| 7,550,451 B2 | 6/2009 | Hillisch et al. |

(Continued)

FOREIGN PATENT DOCUMENTS

| | | |
|---|---|---|
| CA | 2280041 C | 8/1998 |
| EP | 0057115 A2 | 4/1982 |

(Continued)

OTHER PUBLICATIONS

Fuhrmann et al, "Synthesis and Biological Activity of a Novel, highly Potent Progesterone Receptor Antiagonist," J. Med. Chem., vol. 43, pp. 5010-5016 (2000).

(Continued)

*Primary Examiner* — Barbara P Badio
(74) *Attorney, Agent, or Firm* — Karen B. King; Thomas C. Blankinship

(57) ABSTRACT

The invention relates to 17-hydroxy-13-methyl-17-pentafluoroethyl-11-acyloxyalkylenephenyl-dodecahydrocyclopenta[a]phenanthren-3-one derivatives of the formula I with progesterone-antagonizing action and to processes for preparation thereof, to use thereof for treatment and/or prophylaxis of disorders and to the use thereof for production of medicaments for treatment and/or prophylaxis of disorders, especially of fibroids of the uterus (myomas, uterine leiomyomas), endometriosis, heavy menstrual bleeds, meningiomas, hormone-dependent breast cancers and complaints associated with the menopause, or for fertility control and emergency contraception.

20 Claims, No Drawings

(56) References Cited

U.S. PATENT DOCUMENTS

| | | |
|---|---|---|
| 7,799,770 B2 | 9/2010 | Grawe et al. |
| 7,910,573 B2 | 3/2011 | Beckmann et al. |
| 8,053,426 B2 | 11/2011 | Fuhrmann et al. |
| 2001/0016578 A1 | 8/2001 | Spicer et al. |
| 2002/0045774 A1 | 4/2002 | Schwede et al. |
| 2002/0143000 A1 | 10/2002 | Hegele-Hartung et al. |
| 2003/0069434 A1 | 4/2003 | Bohlmann et al. |
| 2003/0191099 A1 | 10/2003 | Bohlmann et al. |
| 2004/0006241 A1 | 1/2004 | Grawe et al. |
| 2004/0048841 A1 | 3/2004 | Hoffmann et al. |
| 2004/0157811 A1 | 8/2004 | Lichtner et al. |
| 2005/0080060 A1 | 4/2005 | Schwede et al. |
| 2005/0277769 A1 | 12/2005 | Burton et al. |
| 2007/0105828 A1 | 5/2007 | Joshi et al. |
| 2009/0075989 A1 | 3/2009 | Schwede et al. |
| 2011/0112057 A1 | 5/2011 | Fuhrmann et al. |
| 2012/0149670 A1 | 6/2012 | Schwede et al. |
| 2012/0184515 A1 | 7/2012 | Klar et al. |
| 2012/0190660 A1 | 7/2012 | Klar et al. |
| 2012/0258941 A1 | 10/2012 | Klar et al. |
| 2012/0316145 A1 | 12/2012 | Klar et al. |
| 2013/0005697 A1 | 1/2013 | Schwede et al. |
| 2013/0072464 A1 | 3/2013 | Schwede et al. |

FOREIGN PATENT DOCUMENTS

| | | |
|---|---|---|
| EP | 0411733 B1 | 2/1991 |
| EP | 0676203 A1 | 10/1995 |
| EP | 909764 A1 | 4/1999 |
| EP | 0970103 B1 | 4/2002 |
| EP | 1862468 | 12/2007 |
| IN | 978/MUM/2005 | 8/2005 |
| JP | H11171774 A | 6/1999 |
| WO | 9603130 A1 | 2/1996 |
| WO | 9615794 | 5/1996 |
| WO | 9623503 A1 | 8/1996 |
| WO | 98/05679 A2 | 2/1998 |
| WO | 9807740 | 2/1998 |
| WO | 98/26783 A1 | 6/1998 |
| WO | 98/34947 A1 | 8/1998 |
| WO | 99/53924 A1 | 10/1998 |
| WO | 9933855 | 7/1999 |
| WO | 0147490 A1 | 7/2001 |
| WO | 02/32429 A2 | 4/2002 |
| WO | 03045972 A1 | 6/2003 |
| WO | 03/093292 | 11/2003 |
| WO | 2004014935 A1 | 2/2004 |
| WO | 2006/010097 A2 | 1/2006 |
| WO | 2008/058767 A1 | 5/2008 |
| WO | 2009138186 A2 | 11/2009 |
| ZA | 97/7482 | 2/1998 |

OTHER PUBLICATIONS

Steinauer et al., "Systematic review of mifepristone for the treatment of uterine leiomyomata," Obstet Gynecol, vol. 103, No. 6, pp. 1331-1336 (Jun. 2004).

Chwalisz et al., "A randomized, controlled trial of asoprisnil, a novel selective progesterone receptor modulator, in women with uterine leiomyomata," Fertil Steril, vol. 87, No. 6, pp. 1399-1412 (Jun. 2007).

Kettel et al., "Endocrine responses to long-term administration of the antiprogesterone RU486 in patients with pelvic endometriosis," Fertil Steril, vol. 56, No. 3, pp. 402-407 (Sep. 1991).

Kettel et al., "Treatment of endometriosis with the antiprogesterone mifepristone (RU486)," Fertil Steril, vol. 65, No. 1, pp. 23-28 (Jan. 1996).

Kettel et al., "Preliminary report on the treatment of endometriosis with low-dose mifepristone (RU 486),". Am J Obstet Gynecol, vol. 178, No. 6, pp. 1151-1156 (Jun. 1998).

Möller et a., "Investigational developments for the treatment of progesterone-dependent diseases," Expert Opin. Investig. Drugs., vol. 17, No. 4, pp. 469-479 (2008).

Bagaria et al., Low-dose mifepristone in treatment of uterine leiomyoma: A randomised double-blind placebo-controlled clinical trial, The Royal Australian and New Zealand College of Obstetricians and Gynaecologists, vol. 49, pp. 77-83 (2009).

Murphy et al., "Regression of Uterine Leiomyomata in Response to the Antiprogesterone RU 486," J. Clin. Endocrinol. Metab., vol. 76, No. 2, pp. 513-517 (1993).

Bohl et al, "Molecular mechanics and X-ray crystal structure investigations on conformations of 11β substituted 4,9-dien-3-one steroids," J. Mol. Graphics, vol. 7, pp. 122-153 (Sep. 1989).

Braga et al., "3.3 Crystal Polymorphism: Challenges at the Crossroads of Science and Technology," Making Crystals By Design (Dario Braga and Fabrizia Grepioni eds., Wiley-VCH Verlag GmbH & Co. KgaA, Weinheim, Germany), pp. 293-314 (2007).

Cabri et al., "Polymorphisms and Patent, Market, and Legal Battles: Cefdinir Case Study," Organic Process Research & Devel., vol. 11, No. 1, pp. 64-72 (2007).

Caira, "Crystalline Polymorphism of Organic Compounds," Topics in Current Chemistry, vol. 198, pp. 164-208 (1998).

Davey, "Solvent Effects in Crystallization Processes," Current Topics in Material Science, vol. 8, pp. 429-479.

English Translation of Office Action for European App. No. 06 090 095 dated Jan. 16, 2007 (US 7,910,573 B2).

Braja, "Mifepristone (RU-486), the recently developed antiprogesterone drug and tis analogues," J. Indian Inst. Sci., vol. 81, pp. 287-298 (May-Jun. 2001).

U.S. Appl. No. 13/577,799, 371(c) date Sep. 21, 2012, published as US 2013-0005697.

Maibauer et al., "First human data for ZK 230211 (ZK-PRA), a new progesterone receptor antagonist: a phase I clinical analysis of safety and pharmacokinetics in healthy postmenopausal women," Abstracts-Poster Session IV, 29th Annual San Antonio Breast Cancer Symposium, Dec. 14-17, 2006.

Tellekson et al., "Strategies for Attacking and Defending Pharmaceutical Patents: A Modern Take on 'The Art of War,'" Int. Property & Techn. Law Journal, vol. 17, No. 12, pp. 5-14 (Dec. 2005).

English Language Translation of EP0411733, 1991.
English Language Translation of EP0676203, 1995.
English Language Translation of WO1998/026783, 1998.
English Language Abstract of JP H11171774, 1999.

Vippagunta et al., "Crystalline Solids," Adv. Drug Delivery Reviews, vol. 48, pp. 3-26 (2001).

Patani et al., "Bioisosterism: A Rational Approach in Drug Design," Chem. Rev., vol. 96, pp. 3147-3176 (1996).

Hazra, et al.,"Mifepristone (RU-486), the Recently Developed Antiprogesterone Drug and its Analogues," J. Indian Inst. Sci, May-Jun. 2001, 81:287-298.

Van Geerstein et al., "Structure of the n-Butyl Acetate Solvate of 11β-[4-(Dimethylamino)phenyl]-17β-hydroxy-17α-(1-propynyl)estra-4,9-dien-3-one," Acta Cryst., C42, pp. 1521-1523 (1986).

U.S. Appl. No. 13/578,500 371(c) date Oct. 1, 2012, published as US 2013-0072464.

U.S. Appl. No. 13/384,765, 371(c) date Apr. 5, 2012, published as US 2012-0184515.

U.S. Appl. No. 13/386,420 371(c) date Apr. 5, 2012, published as US 2012-0190660.

U.S. Appl. No. 13/386,031 371(c) Aug. 28, 2012, published as US 2012-0316145.

U.S. Appl. No. 13/386,421 371(c) date Jun. 25, 2012, published as US 2012-0258941.

U.S. Appl. No. 13/376,512, 371(c) date Feb. 27, 2012, published as US 2012-0149670.

17-HYDROXY-17-PENTAFLUORETHYL-ESTRA-4,9(10)-DIEN-11-ACYLOXYALKYLENE PHENYL DERIVATIVES, METHODS FOR THE PRODUCTION THEREOF AND USE THEREOF FOR TREATING DISEASES

The invention relates to 17-hydroxy-13-methyl-17-pentafluoroethyl-11-acyloxyalkylenephenyl-dodecahydrocyclopenta[a]phenanthren-3-one derivatives of the formula I with progesterone-antagonising action and to processes for preparation thereof, to use thereof for treatment and/or prophylaxis of disorders and to the use thereof for production of medicaments for treatment and/or prophylaxis of disorders, especially of fibroids of the uterus (myomas, uterine leiomyomas), endometriosis, heavy menstrual bleeds, meningiomas, hormone-dependent breast cancers and complaints associated with the menopause, or for fertility control and emergency contraception.

These compounds are valuable active pharmaceutical ingredients. They can be used, inter alia, for production of pharmaceutical formulations for treatment of fibroids of the uterus or of endometriosis, heavy menstrual bleeds, meningiomas, hormone-dependent breast cancers and complaints associated with the menopause, or for fertility control and emergency contraception. For treatment of uterus fibroids and of endometriosis, the inventive compounds can also be administered sequentially in combination with gestagens. Within such a treatment regime, the inventive compounds could be administered over a period of 1-6 months, followed by a pause in treatment or sequential treatment with a gestagen over a period of 2-6 weeks, or followed by treatment with an oral contraceptive (OC combinations) over the same period.

The efficacy of the inventive compounds as a progesterone receptor antagonist has been shown in vitro in transactivation tests.

Compounds with antagonistic action on the progesterone receptor (competitive progesterone receptor antagonists) were mentioned for the first time in 1982 (RU 486; EP57115) and have been described many times since then. Progesterone receptor antagonists with a fluorinated 17α side chain were published in WO 98/34947 and Fuhrmann et al., J. Med. Chem. 43, 5010-5016 (2000).

The compounds with a fluorinated 17α side chain described in WO 98/34947 generally have very strong antagonistic activity on the progesterone receptor. Compounds which are very potent and are therefore preferred in WO 98/34947 are 11β-(4-acetylphenyl)-20,20,21,21,21-pentafluoro-17-hydroxy-19-nor-17α-pregna-4,9-dien-3-one, 11β-(4-acetylphenyl)-20,20,21,21,21-pentafluoro-17-hydroxy-19-nor-17α-pregna-4-en-3-one and 6'-acetyl-9,11β-dihydro-17β-hydroxy-17α-(1,1,2,2,2-pentafluoroethyl)-4'H-naphth [3',2',1':10,9,11]ester-4-en-3-one. These compounds are converted to various metabolites to a considerable degree in vivo, some of which have strong pharmacological activity, some of them lesser pharmacological activity. The metabolism occurs predominantly at the 4 substituent of the 11-acetylphenyl substituent. WO2008/058767 describes compounds of which at least some are metabolites of the compounds described in WO 98/34947.

The problem addressed by the present invention was originally to be that of providing these active metabolites in the form of a prodrug with defined release, in order to further improve the pharmacokinetic and pharmacodynamic profile of action, and hence to extend and to optimize possible treatments of gynaecological disorders.

Some of the inventive compounds were found to be stable and nevertheless highly active under physiological conditions, and so it was also possible to provide novel competitive progesterone receptor antagonists.

The present invention relates to 17-hydroxy-13-methyl-17-pentafluoroethyl-11-acyloxyalkylenephenyl-dodecahydrocyclopenta[a]phenanthren-3-one derivatives with the general chemical formula I:

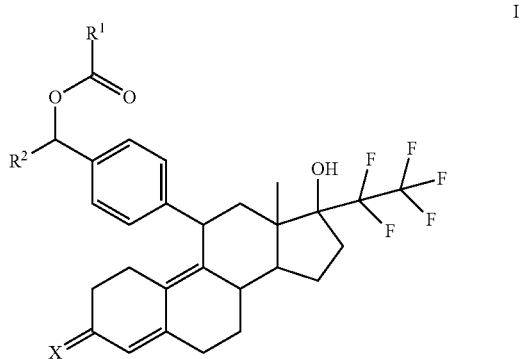

in which
X is oxygen or an $NOR^3$ or $=NNHSO_2R^3$ group,
$R^1$ is $C_1$-$C_{10}$-alkyl, $(CH_2)_n$—Y or $CHR^4NR^5PG$,
$R^2$ is hydrogen or $C_1$-$C_{10}$-alkyl,
$R^3$ is hydrogen, $C_1$-$C_{10}$-alkyl, aryl or $C_7$-$C_{20}$-aralkyl,
n is 1 to 10,
Y is hydrogen, aryl or heteroaryl,
$R^4$, $R^5$ are each independently hydrogen, $C_1$-$C_{10}$-alkyl, $C_7$-$C_{10}$-aralkyl, or together are a $(CH_2)_m$— or a $CH_2CHOHCH_2$ group,
$R^6$ is hydrogen, $C_1$-$C_{10}$-alkyl, aryl or $C_7$-$C_{20}$-aralkyl,
m is 3 or 4 and
PG is hydrogen or an amino protecting group
  and the salts, solvates or solvates of the salts thereof, including all crystal polymorphs, the α-, β- or γ-cyclodextrin clathrates, and the compounds encapsulated with liposomes.

Depending on their structure, the inventive compounds of the general formula I can exist in stereoisomeric forms (enantiomers, diastereomers). The invention therefore encompasses the enantiomers or diastereomers and the particular mixtures thereof, including the racemates. It is possible to isolate the stereoisomerically homogeneous constituents from such mixtures of enantiomers and/or diastereomers in a known manner.

Each of the substituents on the steroid backbone mentioned may be either in an α position or in a β position. In addition, it is also possible for the substituents on the steroid backbone which contain a double bond and in which the double bond bears at least one non-hydrogen substituent on each atom to be present either in E or Z configuration.

When the inventive compounds can occur in tautomeric forms, the present invention encompasses all tautomeric forms.

Preferred salts in the context of the present invention are physiologically compatible salts of the inventive compounds. Also included, however, are salts which are themselves unsuitable for pharmaceutical applications but can be used, for example, for the isolation or purification of the inventive compounds.

Physiologically compatible salts of the inventive compounds include—when a basic function is present—salts with inorganic or organic acids, especially of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid or benzoic acid. Physiologically compatible salts of the inventive compounds include—when an acidic acid function is present—alkali metal salts, alkaline earth metal salts or ammonium salts, as obtainable by reaction with corresponding inorganic or organic bases. Preferred examples include alkali metal salts (e.g. sodium and potassium salts), alkaline earth metal salts (e.g. calcium and magnesium salts) and ammonium salts derived from ammonia or organic amines having 1 to 16 carbon atoms, preferred examples being ethylamine, diethylamine, triethylamine, ethyldiisopropylamine, monoethanolamine, diethanolamine, triethanolamine, dicyclohexylamine, dimethylaminoethanol, procain, dibenzylamine, N-methylmorpholine, arginine, lysine, ethylenediamine, N-methylpiperidine, N-methyl-glucamine, D-methylglucamine, ethylglucamine, 1,6-hexadiamine, glucosamine, N-methylglycine, 2-amino-1,3-propanediol, tris(hydroxymethyl)aminomethane or 1-amino-2,3,4-butanetriol.

Solvates in the context of the invention refer to those forms of the inventive compounds which, in the solid or liquid state, exhibit adduct formation with solvent molecules. The solvent may be in a stoichiometric or else nonstoichiometric ratio. In the case of stoichiometric solvates, reference is also made to hemi- (semi-), mono-, sesqui-, di-, tri-, tetra-, pentasolvates, etc. Hydrates are a specific form of the solvates in which the coordination is with water.

In the context of the present invention, the substituents, unless specified otherwise, are each defined as follows:

Alkyl represents straight- or branched-chain alkyl groups having 1-6 carbon atoms, for example methyl, ethyl, propyl, isopropyl, n-butyl, sec-butyl, isobutyl, tert-butyl, n-pentyl, isopentyl, neopentyl, hexyl, heptyl, octyl, nonyl and decyl.

Aryl is a mono- to tricyclic aromatic substituted or unsubstituted carbocyclic radical, for example phenyl, naphthyl, which may be mono- or polysubstituted by halogen (F, Cl, Br, I), OH, O-alkyl, $CO_2H$, $CO_2$-alkyl, $NH_2$, $NH(C_1-C_{10}$-alkyl), $N(C_1-C_{10}$-alkyl)$_2$, especially $N(CH_3)_2$, $NO_2$, $N_3$, CN, $C_1-C_{10}$-alkyl, $C_2-C_{10}$-alkylene, $C_2-C_{10}$-alkynyl, $C_1-C_{10}$-perfluoroalkyl, $C_1-C_{10}$-acyl, $C_1-C_{10}$-acyloxy groups.

Heteroaryl is an aromatic mono- or bicyclic radical having generally 5 to 10 and preferably 5 to 6 ring atoms and up to 5, preferably up to 4, heteroatoms from the group of S, O and N, preferred examples being benzofuranyl, benzothiophenyl, quinolinyl, furyl, imidazolyl, indazolyl, indolyl, isoquinolinyl, oxazolyl, pyridazinyl, pyridyl, pyrimidyl, pyrrolyl, thiazolyl, thienyl, pyrazolyl, isoxazolyl, pyrazinyl, quinolyl or tetrazolyl, which may be monosubstituted by $C_1-C_4$-alkyl.

Aralkyl represents aralkyl groups which may contain up to 14 carbon atoms, preferably 6-10 carbon atoms, in the ring and 1-8, preferably 1-4, carbon atoms in the alkyl chain. Useful aralkyl radicals include, for example, benzyl, phenylethyl, naphthylmethyl, naphthylethyl, furylmethyl, thienylethyl, pyridylpropyl. The rings may be mono- or polysubstituted by halogen, OH, O-alkyl, $CO_2H$, $CO_2$-alkyl, $NH_2$, $NH(C_1-C_{10}$-alkyl), $N(C_1-C_{10}$-alkyl)$_2$, $NO_2$, $N_3$, CN, $C_1-C_{20}$-alkyl, $C_1-C_{10}$-perfluoroalkyl, $C_1-C_{20}$-acyl, $C_1-C_{20}$-acyloxy groups.

Amino protecting groups are standard groups for protection of amino functions, for example tert-butoxycarbonyl (t-BOC) or allyloxycarbonyl.

When radicals in the inventive compounds are substituted, the radicals, unless specified otherwise, may be mono- or polysubstituted. In the context of the present invention, all radicals which occur more than once are each defined independently of one another. Substitution by one, two or three identical or different substituents is preferred. Very particular preference is given to substitution by one substituent.

Preference is given to compounds of the formula (I) in which $R^1$ is $C_1-C_{10}$-alkyl, preferably $C_1-C_6$-alkyl, more preferably $C_1-C_5$-alkyl, most preferably methyl, isopropyl, isobutyl and neopentyl, and salts, solvates or solvates of the salts thereof, the α-, β- or γ-cyclodextrin clathrates, and the compounds encapsulated with liposomes.

Preference is likewise given to compounds of the formula (I) in which $R^1$ is $(CH_2)_n$—Y where n=1-10 and Y is an aromatic mono- or bicyclic radical having generally 5 to 10 ring atoms and having up to 5 heteroatoms from the group of S, O and N, preferably $(CH_2)_n$—Y where n=1-5 and Y is an aromatic mono- or bicyclic radical having generally 5 to 9 ring atoms with up to 4 heteroatoms from the group of S, O and N, more preferably n=1-3 and Y=imidazolyl, thiazolyl or pyridyl, and salts, solvates or solvates of the salts thereof, the α-, β- or γ-cyclodextrin clathrates, and the compounds encapsulated with liposomes.

Preference is also given to compounds of the formula (I) in which $R^1$ is an amino acid radical $CHR^4NR^5PG$ where $R^4$=hydrogen, $C_1-C_5$-alkyl, $C_7-C_{10}$-aralkyl, or together with $R^5$ is an optionally hydroxyl-substituted propylene or butylene group, $R^5$=hydrogen and PG is $C_1-C_5$-acyl or $C_1-C_5$-alkyloxycarbonyl, $C_3-C_5$-alkenyloxycarbonyl, preferably $R^4$=hydrogen, $C_1-C_4$-alkyl, $C_7-C_8$-aralkyl, or together with $R^5$ is an optionally hydroxyl-substituted propylene group, $R^5$=hydrogen and PG is $C_1-C_5$-acyl or $C_1-C_5$-alkyloxycarbonyl, $C_3-C_5$-alkenyloxycarbonyl, more preferably $R^4$=hydrogen, methyl, isopropyl, isobutyl, benzyl or together with $R^5$ is a propylene group or hydroxypropylene group, $R^5$=hydrogen and PG is acetyl, propionyl, butyryl, isopropionyl, isobutyryl or methoxycarbonyl, ethoxycarbonyl, isopropoxycarbonyl, tert-butoxycarbonyl or allyloxycarbonyl, and salts, solvates or solvates of the salts thereof, the α-, β- or γ-cyclodextrin clathrates, and the compounds encapsulated with liposomes.

Particular preference is also given to the compounds of the formula Ia

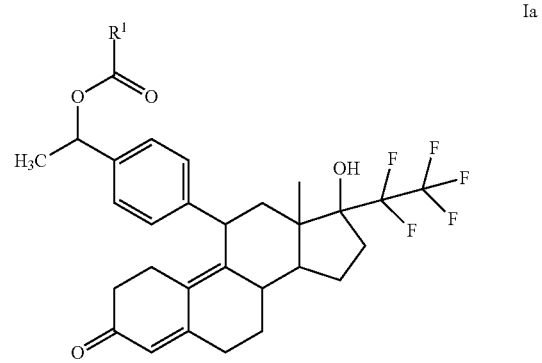

Ia in which
$R^1$ is $C_1-C_{10}$-alkyl, $(CH_2)_n$—Y where n=1-10 or $CHR^4NR^5PG$,
$R^4$, $R^5$ are each independently hydrogen, $C_1-C_{10}$-alkyl, $C_7-C_{10}$-aralkyl, or together are a $(CH_2)_m$— where m=3 or 4 or a $CH_2CHOHCH_2$— group, PG is hydrogen or an amino protecting group
Y is aryl or heteroaryl,
and the salts, solvates or solvates of the salts thereof.

Very particular preference is given to the compounds of the formula Ia in which $R^1$ is methyl, isopropyl, isobutyl or neopentyl, especially the compounds:

acetic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 1)

isobutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 2)

3-methylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 3)

3,3-dimethylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 4).

Very particular preference is likewise given to the compounds of the formula Ia in which $R^1$ is $(CH_2)_2$—Y and Y is 2-methylimidazol-1-yl or thiazol-1-yl, especially the compounds:

3-(2-methylimidazol-1-yl)propionic acid (S)-1-[4-((8S,11R,13S,14S,17S)-17-hydroxy-13-methyl-3-oxo-17-pentafluoroethyl-2,3,6,7,8,11,12,13,14,15,16 17-dodecahydro-1H-cyclopenta[a]phenanthren-11-yl)phenyl]ethyl ester (Ex. 14)

3-(2-methylimidazol-1-yl)propionic acid (R)-1-[4-((8S,11R,13S,14S,17S)-17-hydroxy-13-methyl-3-oxo-17-pentafluoroethyl-2,3,6,7,8,11,12,13,14,15,16 17-dodecahydro-1H-cyclopenta[a]phenanthren-11-yl)phenyl]ethyl ester (Ex. 14)

3-thiazol-2-ylpropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 15)

Very particular preference is also given to the compounds of the formula Ia in which $R^1$ is $CHR^4NR^5PG$ and $R^4$ is methyl or isopropyl, $R^5$ is hydrogen or $R^4$ together with $R^5$ is a propylene group and PG is hydrogen, tert-butyloxycarbonyl or allyloxycarbonyl, especially the compounds:

(S)-2-tert-butoxycarbonylamino-3-methylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 5)

(R)-2-tert-butoxycarbonylaminopropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 6)

(S)-2-tert-butoxycarbonylaminopropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 7)

(S)-2-aminopropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 8)

(S)-2-allyloxycarbonylaminopropionic acid (R)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 9)

(S)-2-allyloxycarbonylaminopropionic acid (S)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 10)

(S)-pyrrolidine-1,2-dicarboxylic acid 1-tert-butyl ester 2-{(RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl}ester (Ex. 11)

(S)-pyrrolidine-2-carboxylic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 12)

(S)-pyrrolidine-2-carboxylic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester hydrochloride (Ex. 13)

(S)-2-allyloxycarbonylamino-3-methylbutyric acid (R)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (Ex. 16).

The specific radical definitions given in the particular combinations or preferred combinations of radicals are, irrespective of the particular combinations of radicals specified, also replaced as desired by radical definitions of other combinations.

Very particular preference is given to combinations of two or more of the above-mentioned preferred ranges.

Particular preference is likewise given to the inventive compounds with a half-life in human plasma, determined by the method in working example 19, of greater than 100 hours, especially the compounds according to examples 1, 2, 3, 4, 5, 6, 7, 9, 11, 14A, 15 and 16 (cf. Example 19, Table 3).

It has been found that the inventive compounds or derivatives have good progesterone-antagonizing action. In several clinical studies, it has been found that treatment with progesterone receptor antagonists (mifepristone, asoprisnil, Proellex) can lead to significant shrinkage of fibroids of the uterus and to significant reduction of the symptoms associated with these fibroids of the uterus. In addition, it has been found in clinical studies that, during a treatment with the progesterone receptor antagonists mentioned, the symptoms caused by endometriosis (especially pain) can also be distinctly reduced.

To the extent that the preparation of the starting compounds is not described here, they are known to the person skilled in the art or are preparable analogously to known compounds or processes described here. The isomer mixtures can be separated into the individual compounds by customary methods, for example crystallization, chromatography or salt formation. The salts are prepared in a customary manner, by admixing a solution of the compounds of the general chemical formula I with the equivalent amount or an excess of a base or acid which may be in solution, optionally removing the precipitate or working up the solution in a customary manner.

The invention further provides a process for preparing the inventive compounds, wherein the secondary hydroxyl groups are esterified (Ex. 1-7, 9-11 and 14-16). This is optionally followed by protecting group detachment (Ex. 8 and 12).

The resulting compounds of the formula (I) are optionally reacted with the appropriate (i) solvents and/or (ii) bases and/or acids to give the solvates, salts and/or solvates of the salts thereof.

The invention further relates to processes for preparing steroid esters of the formula I, characterized in that compounds of the formula II as described in detail in Examples 1 and 5 are esterified and any protecting groups present in PG are detached as described in detail in Examples 8 and 12. The preparation of the inventive compounds can be illustrated by the following synthesis scheme:

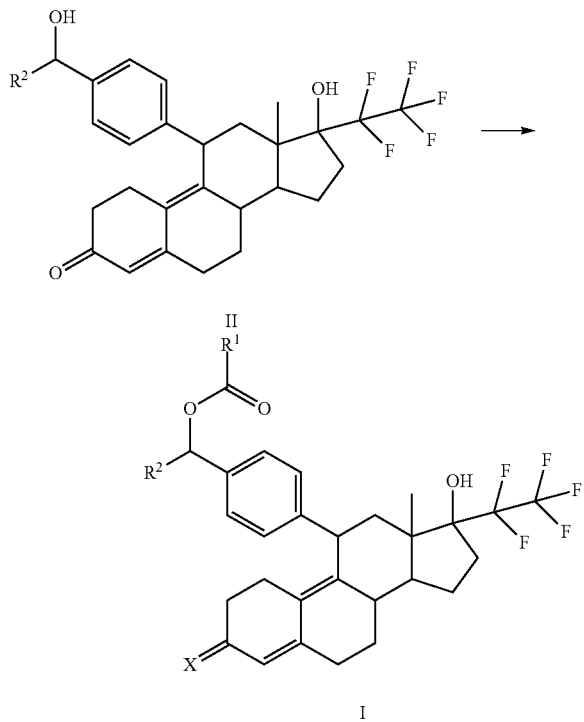

The preparation of a compound of the formula II where $R^2$=methyl is described, for example, in WO 98/34947, Example 13 (page 22). The resulting compounds of the general formula I in which X is an oxygen atom can be converted by reaction with hydroxylamine hydrochloride, alkyloxyamine hydrochlorides or sulphonylhydrazines in the presence of a tertiary amine at temperatures of between −20 and +40° C. to the corresponding E/Z-configured oximes or sulphonylhydrazones thereof (general formula I where X is defined as =$NOR^3$, =$NNHSO_2R^3$). Suitable tertiary bases are, for example, trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), preference being given to pyridine. An analogous process is described, for example, in WO 98/24801.

The radical definitions given above in general terms or specified within areas of preference apply both to the end products of the formula (I) and correspondingly to the starting materials or intermediates required for the preparation of each.

The inventive compounds exhibit an unforeseeable, valuable pharmacological, pharmacokinetic and pharmacodynamic profile of action.

They are therefore suitable for use as medicaments for treatment and/or prophylaxis of disorders in humans and animals.

The pharmaceutical efficacy of the inventive compounds can be explained by the action thereof as a progesterone receptor antagonist, i.e. the antagonizing action thereof on the progesterone receptor.

The present invention further provides for the use of the inventive compounds for treatment and/or prophylaxis of disorders based on hormone-dependent hyperproliferative processes, preferably of gynaecological disorders, especially of fibroids of the uterus, endometriosis or hormone-dependent breast cancers.

The present invention further provides for the use of the inventive compounds for treatment and/or prophylaxis of disorders, especially of the aforementioned disorders.

The present invention further provides the inventive compounds for use in a process for treatment and/or prophylaxis of fibroids of the uterus, of endometriosis and of hormone-dependent breast cancers.

The present invention further provides for the use of the inventive compounds for production of a medicament for treatment and/or prophylaxis of disorders, especially of the aforementioned disorders.

The present invention further provides a method for treatment and/or prophylaxis of disorders, especially of the aforementioned disorders, using 0.1-100 mg of the inventive compounds per day and patient in the treatment of fibroids of the uterus or of endometriosis, and for the contraceptive use, or of 0.1-500 mg of the inventive compounds per day and patient in the event of tumours (e.g. menginioma or hormone-dependent tumours, for example breast cancer) and in emergency contraception.

The present invention further provides medicaments comprising at least one inventive compound and at least one or more than one further active ingredient, especially for treatment and/or prophylaxis of the aforementioned disorders.

For treatment of tumour disorders, it is possible, for example, to either simultaneously or sequentially administer the following active ingredients/active ingredient classes: SERMs, SERDs, antioestrogens, aromatase inhibitors, kinase inhibitors, angiogenesis inhibitors and/or cytostatics, for example from the group of the taxanes, epothilones or platinum compounds.

For treatment of fibroids of the uterus or of endometriosis, the inventive compounds can be combined simultaneously or sequentially with gestagens or combinations of oestrogens and gestagens.

WO 96/15794 (Spicer et al., Balance Pharm. Inc.), WO 96/03130 (Stöckemann et al., Schering AG) and PCT/EP2009/003249 (Möler et al., Bayer Schering Pharma AG) disclose progesterone receptor antagonist/gestagen regimens. Fibroids of the uterus and endometriosis are very suitably treated by optionally repeating regimens in which the progesterone receptor antagonist is administered over a period of two to four months, followed by the administration of the gestagen over a period of one to four weeks. A particularly suitable administration is the optionally repeating 84-day administration of the progesterone receptor antagonist, followed by the 14-day administration of the gestagen.

For treatment of complaints associated with the menopause, one option is a simultaneous or sequential administration of the inventive compounds, for example, with SERMs, SERDs and oestrogens.

SERMs (Selective Estrogen Receptor Modulators) are those compounds which are tissue-selective and have either antioestrogenic or oestrogenic action, for example inhibit the action of oestrogen in the uterus, but have a neutral or oestrogen-like action in the bone. Examples are clomifene, raloxifene, tamoxifene, torimifene, bazedoxifene, lasofoxifene and ormeloxifene.

Selective oestrogen receptor destabilizers (SERDs) are medicaments which antagonise the oestrogen receptor ("pure antioestrogens" without an oestrogenic active component) and lead to degradation of the receptor (for example fulvestrant, ZK-703 and ZK-253 (Hoffmann J et al., J Natl Cancer Inst 2004, 96:210-218), and compounds described in WO 98/007740, WO 99/33855 and WO 03/045972.

Antioestrogens are compounds which antagonise the oestrogen receptor, for example fulvestrant.

Aromatase inhibitors inhibit the enzyme aromatase and hence the aromatisation of androgens in oestrogens. These include anastrozole, letrozole, exemestane, vorozole, formestane and fadrozole.

Kinase inhibitors inhibit enzymes which transfer a phosphate residue from ATP to other substrates, and especially to hydroxyl groups therein, for example sorafenib (Nexavar) or imatinib (Gleevec).

Angiogenesis inhibitors, e.g. avastatin, reduce or block new vessel formation and hence the profusion of a tumour.

Cytostatics, e.g. cis-platin, taxol, Taxotere, sagopilone, ixabepilone, are natural or synthetic substances which drive tumour cells to apoptosis.

Gestagens in the context of the present invention are understood to mean either natural progesterone itself or synthetic derivatives which, like progesterone itself, bind to the progesterone receptor and inhibit ovulation in doses above the ovulation-inhibiting dose. Examples of synthetic derivatives include drospirenone, gestodene, levonorgestrel, cyproterone acetate, desogestrel and 3-ketodesogestrel, norethisterone, norethisterone acetate and dienogest.

Combinations of gestagens and oestrogens are active ingredient combinations present in the oral contraceptive known per se, for example Yasmin, Femovan, Triquilar, Marvelon, YAZ etc.

The inventive compounds can act systemically and/or locally. For this purpose, they can be administered in a suitable manner, for example by an oral, intrauterine, intravaginal, parenteral, pulmonary, nasal, sublingual, lingual, buccal, rectal, dermal, transdermal, conjunctival or otic route, or as an implant or stent.

"Intrauterine" means especially administration by means of an IUS (intrauterine system) or IUD (intrauterine device). One method of intravaginal administration is by means of an IVR (vaginal ring).

Intrauterine or intravaginal administration forms (cf., for example, WO 01/47490, especially page 1 line 10 to page 5 line 13 and page 7 line 19 to page 58 line 6, or for vaginal rings: WO 06/010097, especially page 10 line 22 to page 14 line 28) may comprise the inventive compounds and nonsilicone and/or silicone polymers, especially also siloxane-based elastomers (cf. WO 01/47490, especially page 7 line 19—page 15 line 15).

For these administration routes, the inventive compounds can be administered in suitable administration forms.

Suitable administration forms for oral administration are those which release the inventive compounds in a rapid and/or modified manner, work according to the prior art and contain the inventive compounds in crystalline and/or amorphous and/or dissolved form, for example tablets (uncoated or coated tablets, for example with enteric or retarded-dissolution or insoluble coatings which control the release of the inventive compound), tablets or films/wafers which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilisates or sterile powders.

Various methods for increasing the solubility of sparingly soluble active ingredients for production of parenteral formulations are described in EP 1674098 (Examples 1 to 3). U.S. Pat. No. 6,407,079 describes injectable formulations in which β-cyclodextrins partially modified by hydroxyethyl, hydroxypropyl, dihydroxypropyl, methyl or ethyl ethers are used for formulation of active ingredients. The resulting inclusion or adhesion complex has better water solubility than the active ingredient. Sulphoalkyl ether cyclodextrins and derivatives thereof for improving the solubility of water-insoluble active ingredients are described in U.S. Pat. No. 5,376,645 and U.S. Pat. No. 5,134,127.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms listed. This can be accomplished in a manner known per se by mixing with inert nontoxic pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and taste and/or odour correctors.

The present invention further provides medicaments which comprise at least one inventive compound, typically together with one or more inert nontoxic pharmaceutically suitable excipients, and for the use thereof for the aforementioned purposes.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are percentages by weight unless stated otherwise; parts are parts by weight. Solvent ratios, dilution ratios and concentration figures for liquid/liquid solutions are each based on volume.

The examples which follow serve to illustrate the invention without restricting it in any way.

Example 1

Acetic acid (R)-1-[4-((8S,11R,13S,14S,17S)-17-hydroxy-13-methyl-3-oxo-17-pentafluoroethyl-2,3,6,7,8,11,12,13, 14,15,16,17-dodecahydro-1H-cyclopenta[a]-phenanthren-11-yl)phenyl]ethyl ester (A) and (S)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (B)

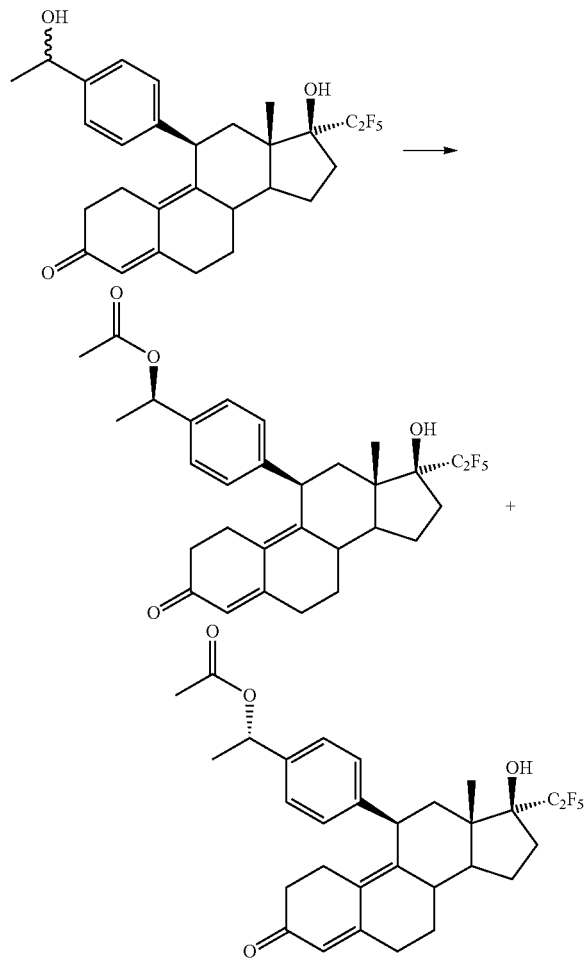

The solution of 1.5 g (2.94 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one (cf. WO 98/34947, Example 13, page 22) in 20 ml of pyridine was admixed with 10 ml of acetic anhydride and stirred at 23° C. for 2.5 hours. The mixture was poured onto saturated sodium hydrogencarbonate solution and extracted repeatedly with dichloromethane, and the combined organic extracts were washed with saturated sodium chloride solution and dried over sodium sulphate. The residue obtained after filtration and removal of solvent was purified by crystallization from diisopropyl ether. 1.47 g (91%) of the title compounds A and B were isolated as a colourless crystalline solid. The isomers were separated by chromatography.

$^1$H NMR (CDCl$_3$) of A: δ=0.59 (3H), 1.27 (3H), 1.39-1.55 (2H), 1.50 (3H), 1.72-1.86 (3H), 2.00-2.10 (2H), 2.22-2.65 (9H), 2.72 (1H), 4.43 (1H), 5.78 (1H), 5.85 (1H), 7.15 (2H), 7.25 (2H) ppm.

$^1$H NMR (CDCl$_3$) of B: δ=0.59 (3H), 1.27 (3H), 1.39-1.55 (2H), 1.50 (3H), 1.72-1.86 (3H), 2.0-2.10 (2H), 2.22-2.65 (9H), 2.72 (1H), 4.43 (1H), 5.77 (1H), 5.85 (1H), 7.14 (2H), 7.25 (2H) ppm.

Example 2

Isobutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]-phenanthren-11-yl)phenyl]ethyl ester

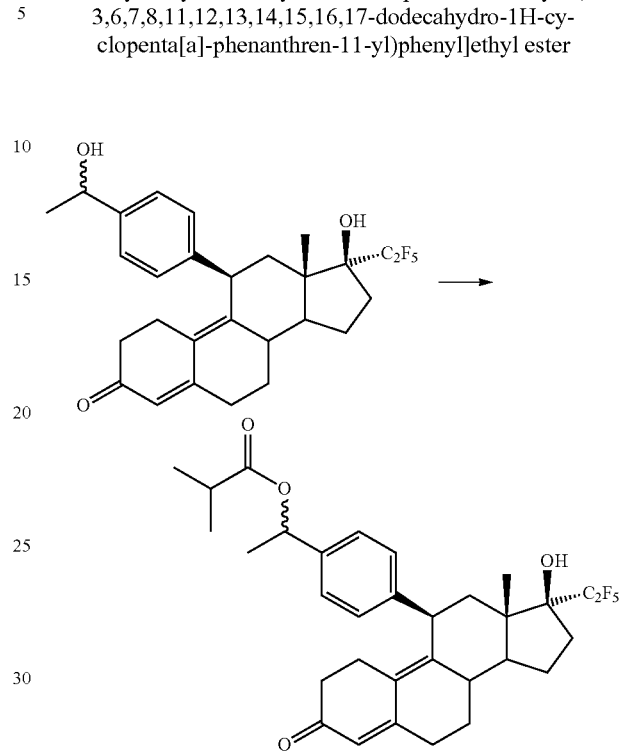

In analogy to Example 1, 150 mg (0.29 mmol) of (8S,11R,13S,14S,17S)-17-hydroxy-11-[4-((RS)-1-hydroxyethyl)phenyl]-1 3-methyl-17-pentafluoroethyl-1,2,6,7,8,11,12,13,14,15,16,17-dodecahydrocyclopenta[a]phenanthren-3-one were converted using isobutyric anhydride and, after workup and purification, 148 mg (87%) of the title compounds were isolated as a colourless foam.

$^1$H NMR (CDCl$_3$): δ=0.58 (3H), 1.10-1.20 (6H), 1.50 (3H), 1.40-1.56 (2H), 1.73-1.87 (3H), 2.00-2.12 (2H), 2.22-2.63 (10H), 2.73 (1H), 4.44 (1H), 5.78 (1H), 5.85 (1H), 7.14 (2H), 7.25 (2H) ppm.

Example 3

3-Methylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester

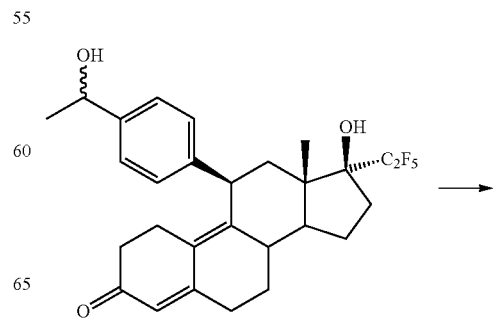

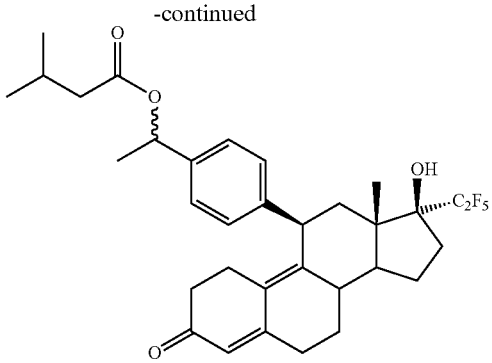

In analogy to Example 1, 150 mg (0.29 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one were converted using isovaleric anhydride and, after workup and purification, 157 mg (90%) of the title compounds were obtained as a colourless foam.

$^1$H NMR (CDCl$_3$): δ=0.58 (3H), 0.86-0.93 (6H), 1.40-1.56 (2H), 1.51 (3H), 1.73-1.86 (3H), 2.00-2.14 (3H), 2.19 (2H), 2.24-2.63 (9H), 2.73 (1H), 4.44 (1H), 5.78 (1H), 5.87 (1H), 7.14 (2H), 7.26 (2H) ppm.

Example 4

3,3-Dimethylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester

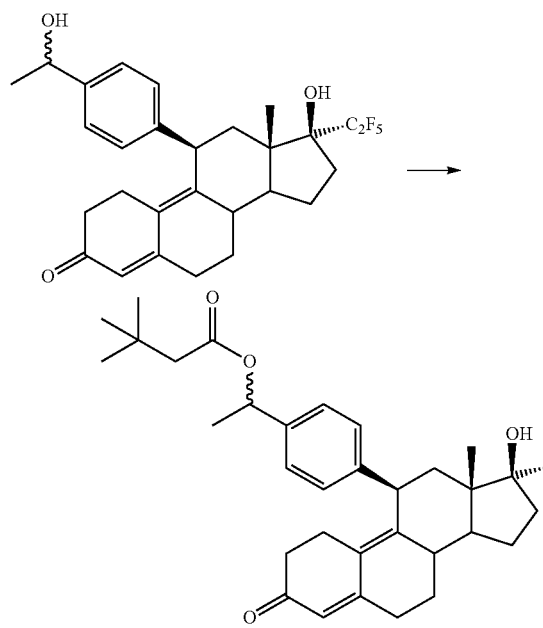

In analogy to Example 1, 150 mg (0.29 mmol) of (8S,11R,13S,14S,17S)-17-hydroxy-11-[4-((RS)-1-hydroxyethyl)phenyl]-1 3-methyl-17-pentafluoroethyl-1,2,6,7,8,11,12,13,14,15,16,17-dodecahydrocyclopenta[a]phenanthren-3-one were converted using 3,3-dimethylbutyryl chloride and, after workup and purification, 113 mg (63%) of the title compounds were isolated as a colourless foam.

$^1$H NMR (CDCl$_3$): δ=0.57 (3H), 0.97 (9H), 1.38-1.57 (2H), 1.52 (3H), 1.72-1.87 (3H), 2.00-2.11 (2H), 2.19 (2H), 2.20-2.64 (9H), 2.73 (1H), 4.43 (1H), 5.78 (1H), 5.87 (1H), 7.14 (2H), 7.28 (2H) ppm.

Example 5

(S)-2-tert-Butoxycarbonylamino-3-methylbutyric acid (RS)-1-[4-((8S,11R,-13S,14S,17S)-17-hydroxy-13-methyl-3-oxo-17-pentafluoroethyl-2,3,6,7,8,11,12,13,14,15,-16,17-dodecahydro-1H-cyclopenta[a]phenanthren-11-yl)phenyl]ethyl ester

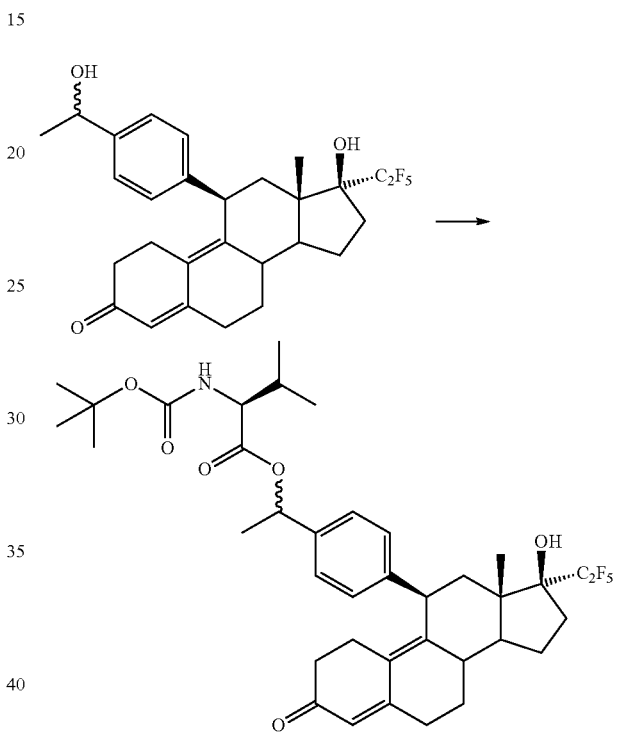

The solution of 300 mg (0.59 mmol) of (8S,11R,13S,14S,17S)-17-hydroxy-11-[4-((RS)-1-hydroxyethyl)phenyl]-1 3-methyl-17-pentafluoroethyl-1,2,6,7,8,11,12,13,14,15,16,17-dodecahydrocyclopenta[a]phenanthren-3-one in 3 ml of pyridine was admixed with 14 mg of 4-dimethylaminopyridine, 383 mg of (S)-2-tert-butoxycarbonylamino-3-methylbutanoic acid and 130 mg of 1-(3-dimethylaminopropyl)-3-ethylcarbodiimide hydrochloride, and the mixture was stirred at 23° C. for 16 hours. The mixture was poured into water and extracted repeatedly with dichloromethane, and the combined organic extracts were washed with water and saturated sodium chloride solution and dried over sodium sulphate. The residue obtained after filtration and solvent removal was purified by chromatography. 314 mg (75%) of the title compounds were isolated as a colourless foam.

$^1$H NMR (CDCl$_3$): δ=0.54+0.59 (3H), 0.63+0.85+0.89+0.95 (6H), 1.43 (9H), 1.53+1.56 (3H), 1.34-1.63 (2H), 1.72-1.87 (3H), 2.00-2.12 (3H) 2.24-2.65 (9H), 2.73 (1H), 4.22 (1H), 4.44 (1H), 4.96+5.03 (1H), 5.78 (1H), 5.90 (1H), 7.12-7.19 (2H), 7.24-7.30 (2H) ppm.

Example 6

(R)-2-tert-Butoxycarbonylaminopropionic acid (RS)-1-[4-((8S,11R,13S,-14S,17S)-17-hydroxy-13-methyl-3-oxo- 17-pentafluoroethyl-2,3,6,7,8,11,12,13,14,15,16,17-dodecahydro-1H-cyclopenta[a]phenanthren-11-yl)phenyl]ethyl ester

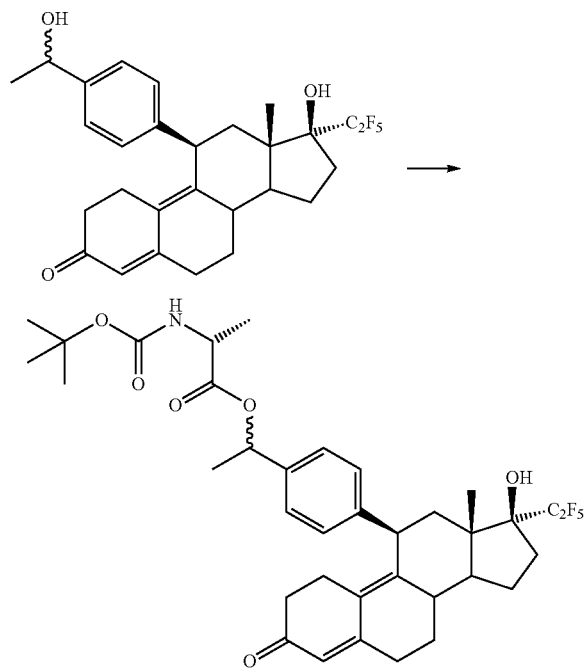

In analogy to Example 5, 300 mg (0.59 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one were converted using (R)-2-tert-butoxycarbonylaminopropionic acid and, after workup and purification, 324 mg (81%) of the title compounds were isolated as a colourless foam.

¹H NMR (CDCl₃): δ=0.57+0.59 (3H), 1.41+1.43 (9H), 1.52+1.54 (3H), 1.29-1.56 (5H), 1.74-1.85 (3H), 2.06 (1H), 2.12 (1H), 2.23-2.62 (9H), 2.73 (1H), 4.31 (1H), 4.43 (1H), 5.03 (1H), 5.78 (1H), 5.89 (1H), 7.15 (2H), 7.24+7.25 (2H) ppm.

Example 7

(S)-2-tert-Butoxycarbonylaminopropionic acid (RS)-1-[4-((8S,11R,13S,-14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester

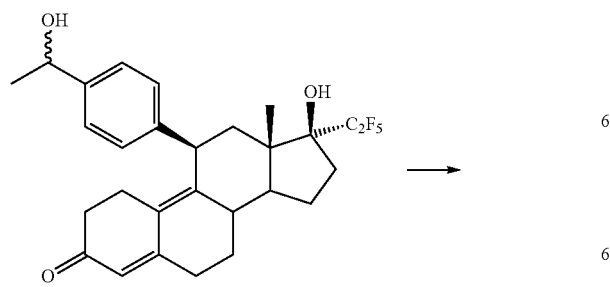

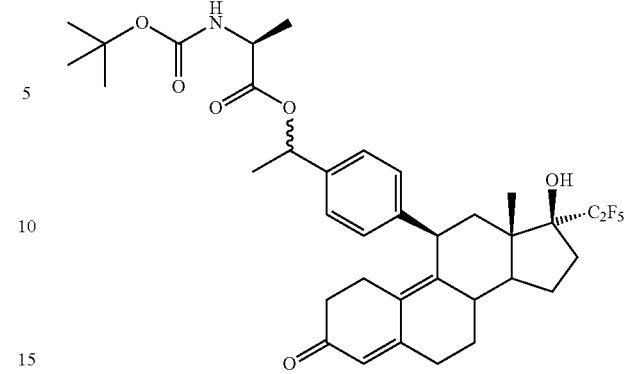

In analogy to Example 5, 300 mg (0.59 mmol) of (8S,11R,13S,14S,17S)-17-hydroxy-11-[4-((RS)-1-hydroxyethyl)phenyl]-1 3-methyl-17-pentafluoroethyl-1,2,6,7,8,11,12,13,14,15,16,17-dodecahydrocyclopenta[a]phenanthren-3-one were converted using (S)-2-tert-butoxycarbonylaminopropionic acid and, after workup and purification, 294 mg (73%) of the title compounds were isolated as a colourless foam.

¹H NMR (CDCl₃): δ=0.57+0.59 (3H), 1.42+1.43 (9H), 1.52+1.54 (3H), 1.29-1.56 (5H), 1.74-1.85 (3H), 2.02-2.13 (2H), 2.22-2.63 (9H), 2.73 (1H), 4.31 (1H), 4.44 (1H), 5.00+5.05 (1H), 5.78 (1H), 5.89 (1H), 7.12-7.18 (2H), 7.22-7.27 (2H) ppm.

Example 8

(S)-2-Aminopropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester

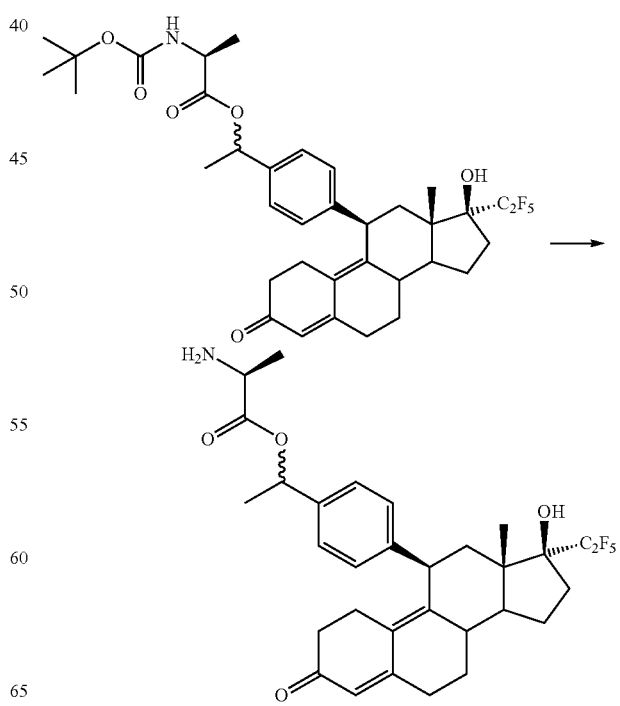

The solution of 50 mg (73 μmol) of the compound prepared according to Example 7 in 0.5 ml of trifluoroacetic acid was stirred at 3° C. for 10 minutes. The mixture was poured onto saturated sodium hydrogencarbonate solution and extracted repeatedly with dichloromethane, and the combined organic extracts were washed with saturated sodium chloride solution and dried over sodium sulphate. The residue obtained after filtration and solvent removal was purified by chromatography. 26 mg (61%) of the title compounds were isolated as a colourless foam.

$^1$H NMR (CD$_3$OD): δ=0.56 (3H), 1.20-1.58 (10H), 1.67-1.84 (3H), 2.01-2.72 (9H), 2.79 (1H), 4.51 (1H), 5.73 (1H), 5.86 (1H), 7.16-7.34 (4H) ppm.

Example 9

(S)-2-Allyloxycarbonylaminopropionic acid (R)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester)

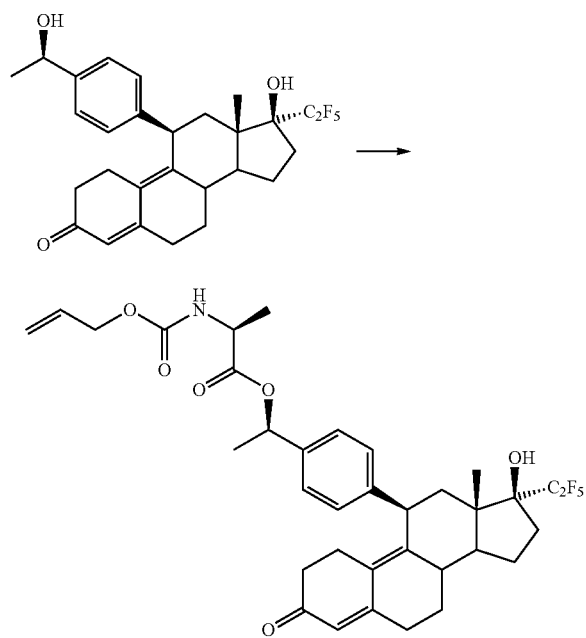

In analogy to Example 5, 150 mg (0.29 mmol) of (8S,11R,13S,14S,17S)-17-hydroxy-11-[4-((R)-1-hydroxyethyl)phenyl]-1 3-methyl-17-pentafluoroethyl-1,2,6,7,8,11,12,13,14,15,16,17-dodecahydrocyclopenta[a]phenanthren-3-one were converted using (S)-2-allyloxycarbonylaminopropanoic acid and, after workup and purification, 140 mg (72%) of the title compound were isolated as a colourless foam.

$^1$H NMR (CDCl$_3$): δ=0.59 (3H), 1.44 (3H), 1.53 (3H), 1.38-1.57 (2H), 1.73-1.87 (3H), 1.99-2.12 (2H), 2.22-2.65 (9H), 2.73 (1H), 4.37 (1H), 4.44 (1H), 4.55 (2H), 5.20 (1H), 5.24-5.35 (2H), 5.78 (1H), 5.82-5.97 (2H), 7.16 (2H), 7.25 (2H) ppm.

Example 10

(S)-2-Allyloxycarbonylaminopropionic acid (S)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethy lester (B)

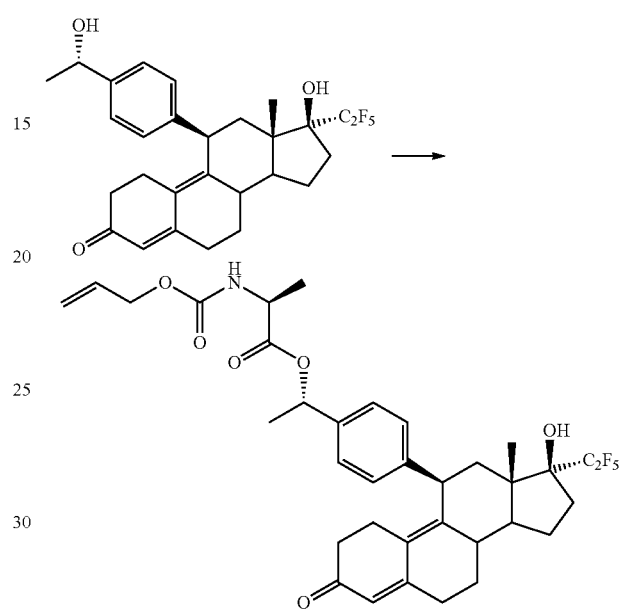

In analogy to Example 5, 150 mg (0.29 mmol) of (8S,11R,13S,14S,17S)-17-hydroxy-11-[4-((S)-1-hydroxyethyl)phenyl]-1 3-methyl-17-pentafluoroethyl-1,2,6,7,8,11,12,13,14,15,16,17-dodecahydrocyclopenta[a]phenanthren-3-one were converted using (S)-2-allyloxycarbonylaminopropanoic acid and, after workup and purification, 87 mg (44%) of the title compound were isolated as a colourless foam.

$^1$H NMR (CDCl$_3$): δ=0.57 (3H), 1.34 (3H), 1.47 (2H), 1.55 (3H), 1.75-1.86 (3H), 2.02-2.11 (2H), 2.23-2.63 (9H), 2.73 (1H), 4.39 (1H), 4.44 (1H), 4.56 (2H), 5.17-5.35 (3H), 5.78 (1H), 5.85-5.96 (2H), 7.15 (2H), 7.24 (2H) ppm.

Example 11

(S)-Pyrrolidine-1,2-dicarboxylic acid 1-tert-butyl ester 2-{(RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl}ester

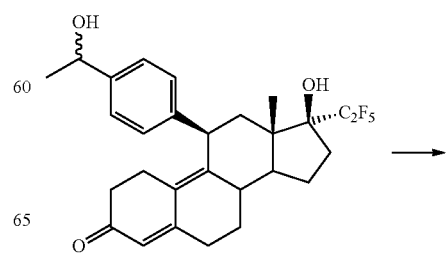

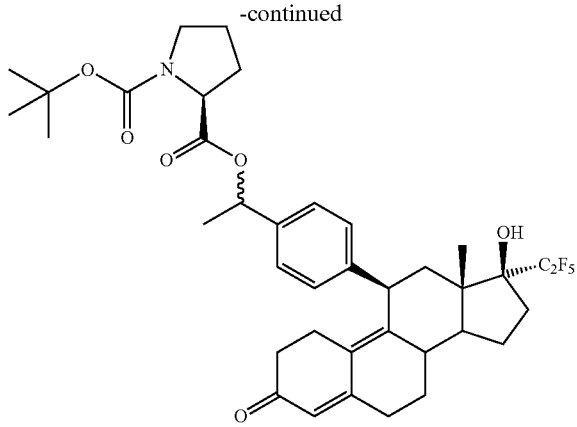

In analogy to Example 5, 330 mg (0.65 mmol) of (8S,11R, 13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one were converted using (S)-pyrrolidine-1,2-dicarboxylic acid 1-tert-butyl ester and, after workup and purification, 356 mg (78%) of the title compounds were isolated as a colourless foam.

$^1$H NMR (CDCl$_3$): δ=0.57 (3H), 1.34-1.56 (14H), 1.74-1.97 (6H), 2.02-2.63 (12H), 2.73 (1H), 3.36-3.57 (2H), 4.24+4.34 (1H), 4.43 (1H), 4.78 (1H), 5.90 (1H), 7.16 (2H), 7.26 (2H) ppm.

Example 12

(S)-Pyrrolidine-2-carboxylic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester

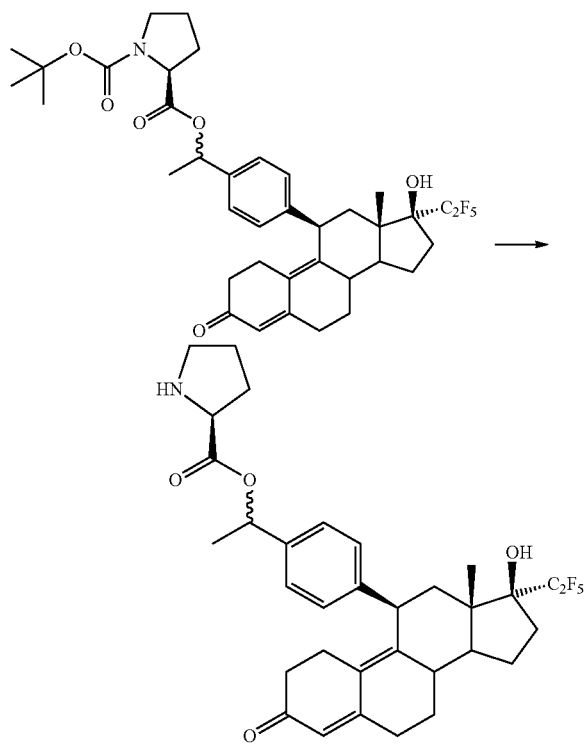

110 mg (0.16 mmol) of the compound prepared according to Example 11 were admixed with 0.44 ml of a 4 molar solution of hydrogen chloride in dioxane and the mixture was stirred at 23° C. for 20 minutes. The mixture was poured onto saturated sodium hydrogencarbonate solution and extracted repeatedly with dichloromethane, and the combined organic extracts were washed with saturated sodium chloride solution and dried over sodium sulphate. The residue obtained after filtration and solvent removal was purified by chromatography. 29 mg (31%) of the title compounds were isolated as a colourless foam.

$^1$H NMR (CDCl$_3$): δ=0.56+0.57 (3H), 1.40-2.64 (21H), 1.52 (3H), 2.73 (1H), 2.87 (1H), 3.05 (1H), 3.75 (1H), 4.44 (1H), 5.78 (1H), 5.89 (1H), 7.15 (2H), 7.25 (2H) ppm.

Example 13

(S)-Pyrrolidine-2-carboxylic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester hydrochloride

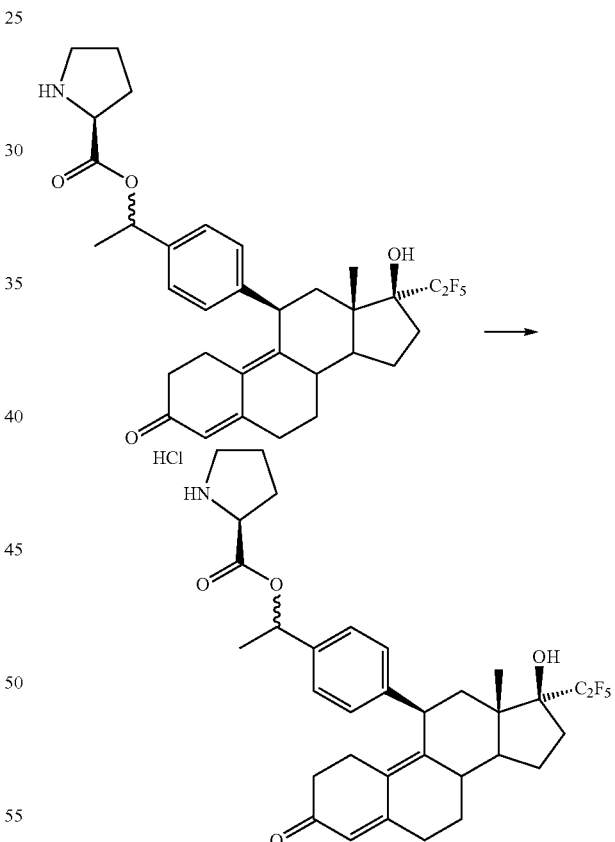

The solution of 29 mg (48 μmol) of the compound prepared according to Example 12 in 0.5 ml of dichloromethane was admixed with 13 μl of a 4 molar solution of hydrogen chloride in dioxane and concentrated to dryness. 30 mg (98%) of the title compounds were isolated as a colourless foam.

$^1$H NMR (CDCl$_3$): δ=0.55+0.58 (3H), 1.38-1.66 (5H), 1.57 (3H), 1.71-1.88 (3H), 1.90-2.66 (13H), 2.73 (1H), 3.44 (2H), 4.31-4.49 (2H), 5.78 (1H), 5.93 (1H), 7.17 (2H), 7.25 (2H) ppm.

Example 14

3-(2-Methylimidazol-1-yl)propionic acid (S)-1-[4-((8S,11R,13S,14S,17S)-17-hydroxy-1 3-methyl-3-oxo-1 7-pentafluoroethyl-2,3,6,7,8,11,12,13,14,15,16,17-dodecahydro-1H-cyclopenta[a]phenanthren-11-yl)phenyl]ethyl ester (A) and 3-(2-methylimidazol-1-yl)propionic acid (R)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester (B)

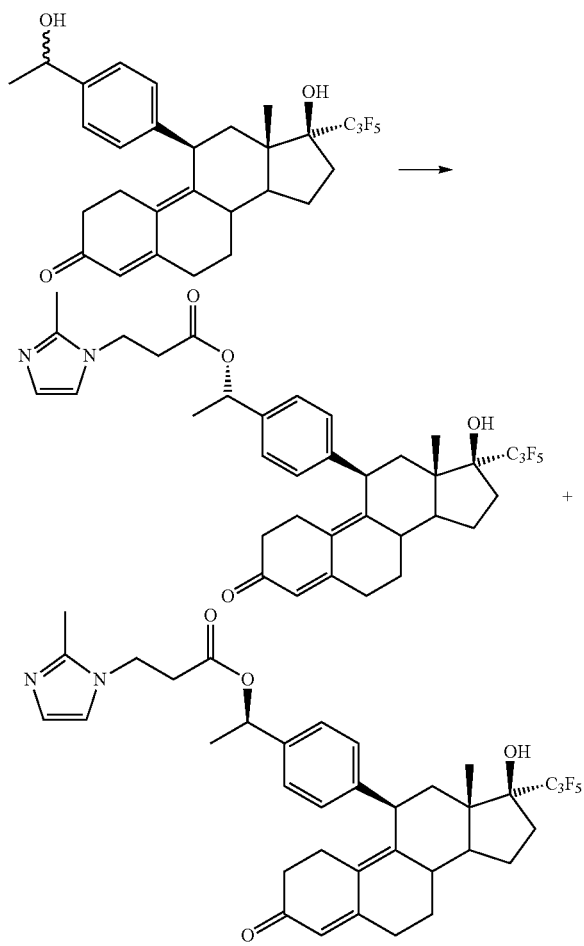

In analogy to Example 5, 150 mg (0.29 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one were converted using 3-(2-methyl-1H-imidazole)propionic acid and, after workup and chromatographic separation, 67 mg (35%) of title compound A and 52 mg (27%) of title compound B were isolated, each as a colourless foam.

$^1$H NMR (CDCl$_3$) of A: δ=0.51 (3H), 1.43-1.57 (2H), 1.53 (3H), 1.69-1.94 (4H), 2.08 (1H), 2.25 (3H), 2.27-2.60 (7H), 2.62-2.76 (3H), 2.82 (1H), 2.97 (1H), 3.90 (1H), 4.29 (1H), 4.39 (1H), 5.64 (1H), 5.79 (1H), 6.87 (1H), 6.92 (1H), 6.96 (2H), 7.00 (2H) ppm.

$^1$H NMR (CDCl$_3$) of B: δ=0.55 (3H), 1.44-1.58 (2H), 1.57 (3H), 1.74-1.92 (4H), 2.09 (1H), 2.29 (3H), 2.25-2.81 (12H), 4.09 (1H), 4.24 (1H), 4.45 (1H), 5.81 (1H), 6.00 (1H), 5.85 (2H), 7.11 (2H), 7.20 (2H) ppm.

Example 15

3-Thiazol-2-ylpropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester

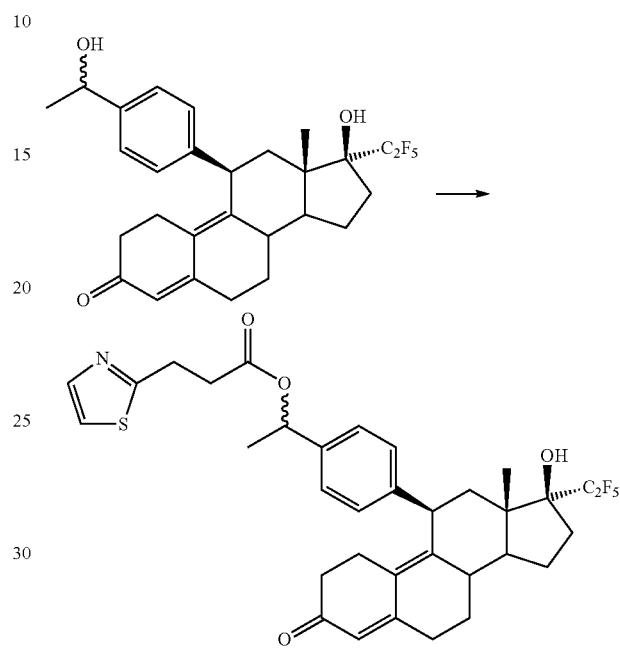

In analogy to Example 5, 150 mg (0.29 mmol) of (8S,11R,13S,14S,17S)-17-hydroxy-11-[4-((RS)-1-hydroxyethyl)phenyl]-1 3-methyl-17-pentafluoroethyl-1,2,6,7,8,11,12,13,14,15,16,17-dodecahydrocyclopenta[a]phenanthren-3-one were converted using 3-(2-thiazolyl)propionic acid and, after workup and purification, 119 mg (62%) of the title compounds were obtained as a colourless foam.

$^1$H NMR (CDCl$_3$): δ=0.59 (3H), 1.40-1.55 (2H), 1.49 (3H), 174-1.86 (3H), 2.06 (1H), 2.18 (1H), 2.23-2.63 (9H), 2.73 (1H), 2.81-2.93 (2H), 3.33 (2H), 4.43 (1H), 5.78 (1H), 5.88 (1H), 7.13 (2H), 7.19 (1H), 7.23 (2H), 7.66 (1H) ppm.

Example 16

(S)-2-Allyloxycarbonylamino-3-methylbutyric acid (RS)-1-[4-((8S,11R,13S,14S,17S)-17-hydroxy-1 3-methyl-3-oxo-1 7-pentafluoroethyl-2,3,6,7,8,11,12,13,14,15,16,17-dodecahydro-1H-cyclopenta[a]phenanthren-11-yl)phenyl]ethyl ester

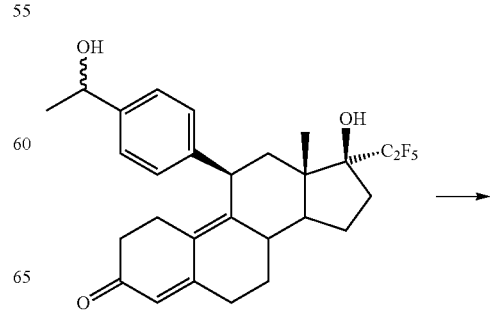

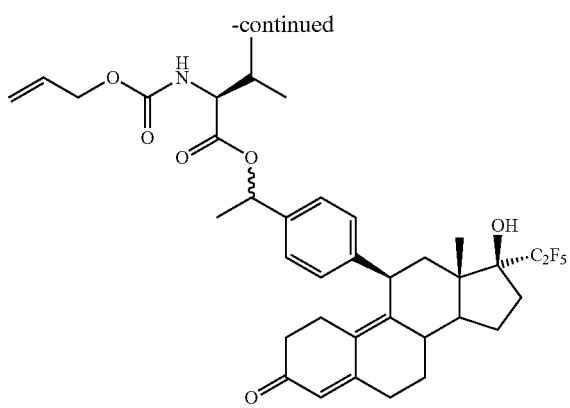

In analogy to Example 5, 400 mg (0.78 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one were converted using (S)-2-allyloxycarbonylamino-3-methylbutyric acid and, after workup and purification, 495 mg (91%) of the title compounds were isolated as a colourless foam.

$^1$H NMR (CDCl$_3$): δ=0.55+0.60 (3H), 0.74-1.26 (7H), 1.37-1.63 (5H), 1.73-1.88 (3H), 2.03-2.66 (11H), 2.74 (1H), 4.30 (1H), 4.40 (1H), 4.57 (2H), 5.16-5.38 (3H), 5.80 (1H), 5.84-6.01 (2H), 7.16 (2H), 7.27 (2H) ppm.

Example 17

Determination of Hydrolytic Stability

The ester to be analyzed was dissolved in each case in a 5:1 mixture of dioxane and buffer solution (pH 1.2, pH 5.0 or pH 8.0) at 23° C. At different times, the content of ester and hydrolysis products (8S,11R,13S,14S,17S)-17-hydroxy-11-[4-((R)-1-hydroxyethyl)phenyl]-13-methyl-17-pentafluoroethyl-1,2,6,7,8,11,12,13,14,15,16,17-dodecahydrocyclopenta[a]phenanthren-3-one and/or (8S,11R,13S,14S,17S)-17-hydroxy-11-[4-((S)-1-hydroxyethyl)phenyl]-1 3-methyl-17-pentafluoroethyl-1,2,6,7,8,11,12,13,14,15,16,17-dodecahydrocyclopenta[a]phenanthren-3-one was determined by HPLC. The test was ended after 24 hours or 192 hours.

TABLE 1

Hydrolytic stability at 23° C. and different pH

| | $t_{1/2}$ [h] @ 23° C. | | |
|---|---|---|---|
| Example | pH = 1.2 | pH = 5.0 | pH = 8.0 |
| 1 | >>24* | >>24* | >>24* |
| 2 | >>24* | >>24* | >>24* |
| 3 | >>24* | >>24* | >>24* |
| 4 | >>24* | >>24* | >>24* |
| 5 | >>192* | >>192* | >>192* |
| 6 | >>24* | >>24* | >>24* |
| 7 | >>24* | >>24* | >>24* |
| 9 + 10 | >>192* | >>192* | >>192* |
| 11 | >>192* | nd** | >>192* |
| 13 | >>192* | nd | >>192* |
| 14 | >>192* | nd | >>192* |
| 15 | >>192* | nd | >>192* |
| 16 | >>192* | nd | >>192* |

*After 24 hours or 192 hours, the content of hydrolysis product is still <1%.
**nd: not determined Example 18

Determination of Hydrolytic Stability in Synthetic Gastric Juice

The esters to be analyzed were dissolved in each case in a buffer solution of pH 1.2 with added pepsin at 37° C. At different times, the content of ester and hydrolysis products (8S,11R,13S,14S,17S)-17-hydroxy-11-[4-((R)-1-hydroxyethyl)phenyl]-1 3-methyl-17-pentafluoroethyl-1,2,6,7,8,11,12,13,14,15,16,17-dodecahydrocyclopenta[a]phenanthren-3-one and/or (8S,11R,13S,14S,17S)-17-hydroxy-11-[4-((S)-1-hydroxyethyl)phenyl]-13-methyl-17-pentafluoroethyl-1,2,6,7,8,11,12,13,14,15,16,17-dodecahydrocyclopenta[a]phenanthren-3-one was determined by HPLC. The test was ended after 24 hours.

TABLE 2

Hydrolytic stability at 37° C. in synthetic gastric juice (pH 1.2)

| Example | $t_{1/2}$ [h] @ 37° C. |
|---|---|
| 1 | 9.6 |
| 2 | >>24* |
| 3 | >>24* |
| 4 | >>24* |
| 5 | 3.0 |
| 6 | 5.4 |
| 7 | 4.4 |

*After 24 hours, the content of hydrolysis product is still <1%.

Example 19

Determination of Stability in Human Plasma and Rat Plasma

A stock solution of 1.0 mg of the substance to be tested in a 9:1 mixture of acetonitrile and dimethyl sulphoxide was prepared. 20 µl of this stock solution were added at 37° C. to 1 ml of human plasma or rat plasma. To determine the content, 100 µl samples were each taken at different times. The enzyme activity was blocked by adding 300 µl of acetonitrile, the samples were centrifuged at 5000 rpm over 10 minutes and, in the supernatant, the content of ester and hydrolysis products (8S,11R,13S,14S,17S)-17-hydroxy-11-[4-((R)-1-hydroxyethyl)phenyl]-1 3-methyl-17-pentafluoroethyl-1,2,6,7,8,11,12,13,14,15,16,17-dodecahydrocyclopenta[a]phenanthren-3-one and/or (8S,11R,13S,14S,17S)-17-hydroxy-11-[4-((S)-1-hydroxyethyl)phenyl]-13-methyl-17-pentafluoroethyl-1,2,6,7,8,11,12,13,14,15,16,17-dodecahydrocyclopenta[a]phenanthrene-3-one was determined by HPLC. The concentration-time curves were used to calculate the degradation kinetics. The stability of the substance tested was reported as the half-life.

TABLE 3

Stability at 37° C. in human plasma and rat plasma

| | $t_{1/2}$ [h] @ 37° C. | |
|---|---|---|
| Example | Human | Rat |
| 1 | 609 | 57.5 |
| 2 | 803 | 33.4 |
| 3 | >1000 | 89 |
| 4 | >1000 | >1000 |
| 5 | >1000 | 156 |

TABLE 3-continued

Stability at 37° C. in human plasma and rat plasma

| | $t_{1/2}$ [h] @ 37° C. | |
|---|---|---|
| Example | Human | Rat |
| 6 | 491 | 43.9 |
| 7 | >1000 | 3.1 |
| 9 | 231 | 0.3 |
| 10 | 22.9 | 3.6 |
| 11 | >1000 | 462 |
| 13 | 9.7 | 5.3 |
| 14A | 190 | 48.5 |
| 14B | 19.8 | 0.8 |
| 15 | 131 | 1.2 |
| 16 | >1000 | 33.2 |

Example 20

Progesterone receptor-antagonistic action in stable transfectants of human neuroblastoma cells (SK-N-MC cells) with the human progesterone A or progesterone B receptor and an MN-LUC reporter construct SK-N-MC cells (human neuroblastoma cells) which have been stably transfected with plasmids expressing the human progesterone receptor B (pRChPR-B-neo) or the human progesterone receptor A (pRChPR-A-neo) and a reporter construct (pMMTV-LUC) were incubated for 24 hours either in the absence (negative control) or in the presence of ascending amounts of the particular test compound (0.01 nmol/l, 0.1 nmol/l, 1 nmol/l, nmol/l, 100 nmol/l and 1 pmol/l), in order to determine the agonistic efficacy. As a positive control of the reporter gene induction, the cells were treated with the synthetic gestagen promegestone (0.01 nmol/l, 0.1 nmol/l, 1 nmol/l, 10 nmol/l, 100 nmol/l and 1 pmol/l). To determine the antagonistic activity, the cells were treated with 0.1 nmol/l promegestone and additionally with ascending amounts of the particular test compound (0.01 nmol/l, 0.1 nmol/l, 1 nmol/l, 10 nmol/l, 100 nmol/l and 1 pmol/l). The activity of the reporter gene LUC (LUC=luciferase) was determined in the cell lysates and measured as RLU (relative light units). All measurements are reported as % efficacy and as $EC_{50}$ and $IC_{50}$ concentrations.

a) Agonistic activity:

None of the compounds mentioned exhibits agonistic activity.

b) Antagonistic activity:

All compounds mentioned exhibit 100% antagonistic activity. The antagonistic potency of the compounds is summarized in Table 4.

TABLE 4

Antagonistic potency of the compounds

| Ex. | PR-A $IC_{50}$ [nM] | PR-B $IC_{50}$ [nM] |
|---|---|---|
| 1 | 0.07 | 0.08 |
| 2 | 0.1 | 0.1 |
| 3 | 0.21 | 0.20 |
| 4 | 0.2 | 0.4 |
| 5 | 0.3 | 0.8 |
| 6 | 0.1 | 0.2 |
| 7 | 0.14 | 0.10 |
| 8 | nd | nd |
| 9 | 0.01 | 0.09 |
| 10 | 0.08 | 0.09 |
| 11 | 0.1 | 0.05 |

TABLE 4-continued

Antagonistic potency of the compounds

| Ex. | PR-A $IC_{50}$ [nM] | PR-B $IC_{50}$ [nM] |
|---|---|---|
| 12 | nd | nd |
| 13 | 0.27 | 0.74 |
| 14A | 0.18 | 0.29 |
| 14B | 0.29 | 0.15 |
| 15 | 0.1 | 0.1 |
| 16 | 0.11 | 0.71 | nd: not determined

The invention claimed is:

1. A compound of the formula I

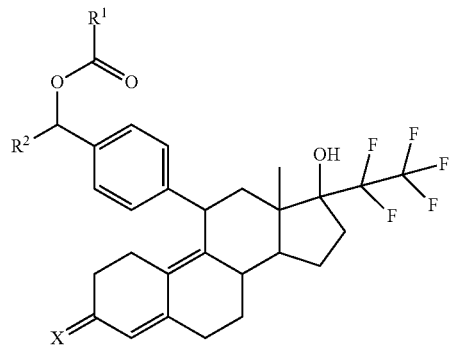

in which

X is oxygen or an $NOR^3$ or $=NNHSO_2R^3$ group, $R^1$ is $C_1$-$C_{10}$-alkyl, $(CH_2)_n$—Y or $CHR^4NR^5PG$, $R^2$ is hydrogen or $C_1$-$C_{10}$-alkyl, $R^3$ is hydrogen, $C_1$-$C_{10}$-alkyl, aryl or $C_7$-$C_{20}$-aralkyl, n is 1 to 10, Y is hydrogen, aryl or heteroaryl, $R^4$, $R^5$ are each independently hydrogen, $C_1$-$C_{10}$-alkyl, $C_7$-$C_{10}$-aralkyl, or together are a $(CH_2)_m$— or a $CH_2CHOHCH_2$— group, m is 3 or 4, PG is hydrogen or an amino protecting group, and the salts or α-, β- or γ-cyclodextrin clathrates thereof.

2. The compound of claim 1, in which $R^1$ is $C_1$-$C_6$-alkyl.

3. The compound of claim 2, wherein $R^1$ is methyl, isopropyl, isobutyl or neopentyl.

4. The compound of claim 1, in which $R^1$ is $(CH_2)_n$—Y where n=1-10 and Y is an aromatic mono- or bicyclic radical with 5 to 10 ring atoms and having up to 5 heteroatoms from the group of S, O and N.

5. The compound of claim 4, in which n=1-5 and Y is an aromatic mono- or bicyclic radical of 5 to 9 ring atoms with up to 4 heteroatoms from the group of S, O and N.

6. The compound of claim 5, in which n=1-3 and Y=imidazolyl, thiazolyl or pyridyl.

7. The compound of claim 1, in which $R^1$ is an amino acid radical $CHR^4NR^5$ PG wherein $R^4$ is hydrogen, $C_1$-$C_5$-alkyl, $C_7$-$C_{10}$-aralkyl, $R^5$ is hydrogen, or $R^4$ together with $R^5$ is an optionally hydroxyl-substituted ethylene or propylene group, and PG is $C_1$-$C_5$-acyl, $C_1$-$C_5$-alkyloxycarbonyl or $C_3$-$C_5$-alkyleneoxycarbonyl.

8. The compound of claim 7, in which $R^4$ is hydrogen, $C_1$-$C_4$-alkyl, $C_7$-$C_8$-aralkyl, $R^5$ is hydrogen or $R^4$ together with $R^5$ is an optionally hydroxyl-substituted ethylene group, and PG is $C_1$-$C_5$-acyl, $C_1$-$C_5$-alkyloxycarbonyl or $C_3$-$C_5$-alkyleneoxycarbonyl.

9. The compound of claim 8, in which $R^4$ is hydrogen, methyl, isopropyl, isobutyl, benzyl, $R^5$ is hydrogen or $R^4$ together with $R^5$ is an ethylene group or hydroxyethylene group, and PG is acetyl, propionyl, butyryl, isopropionyl, isobutyryl, methoxycarbonyl, ethoxycarbonyl, isopropoxycarbonyl, tert-butoxycarbonyl or allyloxycarbonyl.

10. The compound of claim 1 of the formula Ia

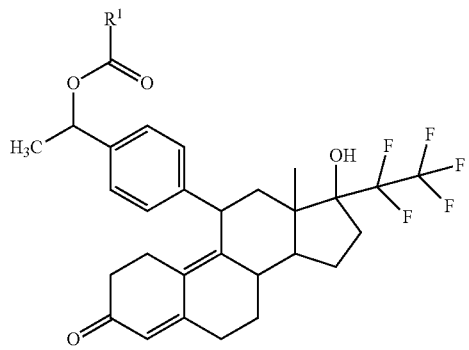

Ia in which $R^1$ is $C_1$-$C_{10}$-alkyl, $(CH_2)_n$—Y where n=1-10 or $CHR^4NR^5PG$, $R^4$, $R^5$ are each independently hydrogen, $C_1$-$C_{10}$-alkyl, $C_7$-$C_{10}$-aralkyl, or together are a $(CH_2)_m$— where m=3 or 4 or a $CH_2CHOHCH_2$— group, PG is hydrogen or an amino protecting group Y is aryl or heteroaryl.

11. The compound of claim 10, in which $R^1$ is methyl, isopropyl, isobutyl or tertbutyl.

12. The compound of claim 10, in which $R^1$ is $(CH_2)_2$—Y and Y is 2-methylimidazol-1-yl or thiazol-1-yl.

13. The compound of claim 10, in which $R^1$ is $CHR^4NR^5PG$ and $R^4$ is methyl or isopropyl, $R^5$ is hydrogen or $R^4$ together with $R^5$ is a —$(CH_2)_3$— group and PG is hydrogen, —COOC$(CH_3)_3$ or —COOCH$_2$CH=CH$_2$.

14. Acetic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

Isobutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

3-methylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

3,3-dimethylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

3-(2-methylimidazol-1-yl)propionic acid (S)-1-[4-((8S,11R,13S,14S,17S)-17-hydroxy-13-methyl-3-oxo-17-pentafluoroethyl-2,3,6,7,8,11,12,13,14,15,16 17-dodecahydro-1H-cyclopenta[a]phenanthren-11-yl)phenyl]ethyl ester;

3-(2-methylimidazol-1-yl)propionic acid (R)-1-[4-((8S,11R,13S,14S,17S)-17-hydroxy-13-methyl-3-oxo-17-pentafluoroethyl-2,3,6,7,8,11,12,13,14,15,16 17-dodecahydro-1H-cyclopenta[a]phenanthren-11-yl)phenyl]ethyl ester;

3-thiazol-2-ylpropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

(S)-2-tert-butoxycarbonylamino-3-methylbutyric acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

(R)-2-tert-butoxycarbonylaminopropionic acid (RS)-1-[4-((8S,11R,13S,14S,17S)-17-hydroxy-13-methyl-3-oxo-17-pentafluoroethyl-2,3,6,7,8,11,12,13,14,15, 16,17-dodecahydro-1H-cyclopenta[a]phenanthren-11-yl)phenyl]ethyl ester;

(S)-2-tert-butoxycarbonylaminopropionic acid (RS)-1-[4-((8S,11R,13S,14S,17S)-17-hydroxy-13-methyl-3-oxo-17-pentafluoroethyl-2,3,6,7,8,11,12,13,14,15, 16,17-dodecahydro-1H-cyclopenta[a]phenanthren-11-yl)phenyl]ethyl ester;

(S)-2-aminopropionic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

(S)-2-allyloxycarbonylaminopropionic acid (R)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

(S)-2-allyloxycarbonylaminopropionic acid (S)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

(S)-pyrrolidine-1,2-dicarboxylic acid 1-tert-butyl ester 2-{(RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl}ester;

(S)-pyrrolidine-2-carboxylic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester;

(S)-pyrrolidine-2-carboxylic acid (RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester hydrochloride; or (S)-2-allyloxycarbonylamino-3-methylbutyric acid (R)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethyl ester.

15. The compound of claim 1 with a half-life in human plasma, determined in vitro, of greater than 100 hours.

16. A medicament comprising a compound of claim 1 in combination with one or more inert, non-toxic, pharmaceutically suitable excipients.

17. The medicament of claim 16 further comprising an active ingredient selected from a SERM, a SERD, an anti-oestrogen, an aromatase inhibitor, a kinase inhibitor, an angiogenesis inhibitor or a cytostatic.

18. The medicament according to claim 16 comprising a further active ingredient selected from gestagens or gestagen/oestrogen combinations.

19. A method for controlling fibroids of the uterus, endometriosis, heavy menstrual bleeds, meningiomas, and breast cancers by administering a compound as defined in claim 1 to a patient in need thereof.

20. A method for fertility control or emergency contraception by administering a compound as defined in claim 1 to a patient in need thereof.

* * * * *